United States Patent [19]

Goslee et al.

[11] 3,936,320
[45] Feb. 3, 1976

[54] HEADER
[75] Inventors: David Earl Goslee, White Marsh; Harold Newton Barr, Baltimore, both of Md.
[73] Assignee: Nuclear Battery Corporation, Columbia, Md.
[22] Filed: Jan. 7, 1974
[21] Appl. No.: 431,363

Related U.S. Application Data
[63] Continuation of Ser. No. 189,838, Oct. 18, 1972, abandoned.

[52] U.S. Cl. .................. 136/242; 403/28; 403/179; 403/270; 403/272
[51] Int. Cl. .............................................. H01v 1/00
[58] Field of Search ............ 403/28, 179, 270–272; 29/473.1; 136/242

[56] References Cited
UNITED STATES PATENTS

| | | | |
|---|---|---|---|
| 3,275,359 | 9/1966 | Graff | 403/179 |
| 3,302,961 | 2/1967 | Franklin | 403/272 |
| 3,367,696 | 2/1968 | Langley | 403/270 |
| 3,370,874 | 2/1968 | Scherer et al. | 403/28 |
| 3,385,618 | 5/1968 | Hargis | 403/271 |
| 3,481,638 | 12/1969 | Dryden | 29/473.1 |
| 3,507,979 | 4/1970 | Erkan | 29/473.1 |

FOREIGN PATENTS OR APPLICATIONS

| | | | |
|---|---|---|---|
| 903,824 | 8/1962 | United Kingdom | 403/179 |

Primary Examiner—Verlin R. Pendegrass
Attorney, Agent, or Firm—Fleit & Jacobson

[57] ABSTRACT

Novel header for use in nuclear applications comprised of a base containing at least one bore, a niobium terminal passing through said bore sealed in an alumina plug which, in turn, is sealed in a bore defined in the base.

7 Claims, 8 Drawing Figures

HEADER

This is a continuation of application Ser. No. 189,838, filed Oct. 18, 1972, and now abandoned.

BACKGROUND OF THE INVENTION

There are, at present, several devices implantable within a human body for aiding or supporting a bodily function. For instance, it is well known in the art that cardiac pacemakers have been implanted within the human body and serve as an electric heart pulser. Such devices require a source of energy which must also be implanted within the human body. In the past, chemical batteries have been employed for this purpose. These sources of electrical power have limited lifetimes and may last, on the average, for only one or two years after which a surgical procedure is necessary to replace the device.

Obviously, a person, in whom such a device has been implanted, who is not amenable to withstanding the shocks or stresses that one is subjected to during such surgical procedures, is benefited by any means which can serve to prolong the life of the electrical power supply.

Although it has been suggested that the electrical power supply should be a nuclear energy source and experimental work has been performed in this area, to date, no one has been able to develop a fully reliable and long-lasting nuclear electric power supply to power implantable devices.

SUMMARY OF THE INVENTION

The present invention relates to a microwatt thermoelectric generator, small in size, efficient in operation and which will last for a considerable period of time.

Accordingly, it is the principal object of the present invention to provide a microwatt thermoelectric generator that contains a nuclear power system to produce an electrical output suitable to service implanted electronic systems which generator will operate efficiently and effectively for longer time periods than such batteries or generators as are currently available. The devices of the present invention are intended to have power outputs of 150 microwatts or higher, operating at efficiencies of above 0.5 percent and more likely at 0.75 percent or above. Also, it is a principal object of the present invention to provide a generator as described that will be relatively small in size to be able to be well tolerated by the human body within spaces available for same and which will be extremely reliable in function.

The foregoing is accomplished by providing a unique nuclear power system essentially comprised of two subassemblies. One subassembly consists of an outer casing containing an insulation system and getter and a nuclear fuel capsule, and the other subassembly consists of a thermopile and a closure system. The nuclear fuel capsule may be made part of the other subassembly. The subassemblies are designed to be assembled and sealed at a single weld joint.

In addition to the foregoing broad concept of providing a highly efficient and long-lasting microwatt thermoelectric generator for powering implanted electronic systems, there are several design features of the generator which are unique.

For example, the getter system is considered to be a novel feature. The particular getter system configuration of the present invention enables performance at more efficient total power output from the smallest quantity of nuclear fuel, resulting in the least fuel cost for a generator. This feature gives the added advantage of the lowest possible radiation damage to surrounding tissue. The arrangement of the fuel capsule within the generator is considered to be a novel feature and is arranged to maintain the maximum possible temperature of the getter assembly while, at the same time, not overheating the thermopile. This concept assures maximum efficiency of both components despite quite different operating temperature requirements.

A further feature of the present invention which is considered to be novel is the thermopile assembly and the manner in which it is treated. The construction of the thermopile itself has novel features which give rise to an efficient and reliable unit that maintains its efficiency for considerable time periods while occupying a relatively small volume. The thermopile is comprised of semiconductor thermoelectric elements which, it is known, are inherently brittle and exhibit low strength compared to metals when subjected to tensile or shearing loads. Tensile and shear loading tends to break or crack the semiconductor thermoelectric elements and/or electrical connectors (shoes) thereby causing electrical discontinuity and failure. Such elements, however, have reasonable strength when subjected to compression loading. Accordingly, one of the features of the thermopile mounting is the provision of a support harness to maintain the thermoelectric elements compressively loaded even under loading conditions which would otherwise result in tension or shear stresses.

DETAILED DESCRIPTION OF THE SEVERAL VIEWS OF THE DRAWINGS

The foregoing objects of the invention and novel features are depicted in the accompanying drawings in which:

FIG. 3 is a vertical section of FIG. 2 taken along line 3—3 of FIG. 2;

FIG. 4 is a detail view showing the thermal connection to the thermopile;

FIG. 5 is a detail section taken along line 5—5 of FIG. 4;

FIG. 7 is a sectional view showing the mounting of the fuel capsule; and

DETAILED DESCRIPTION OF A PREFERRED EMBODIMENT

Figure 1:
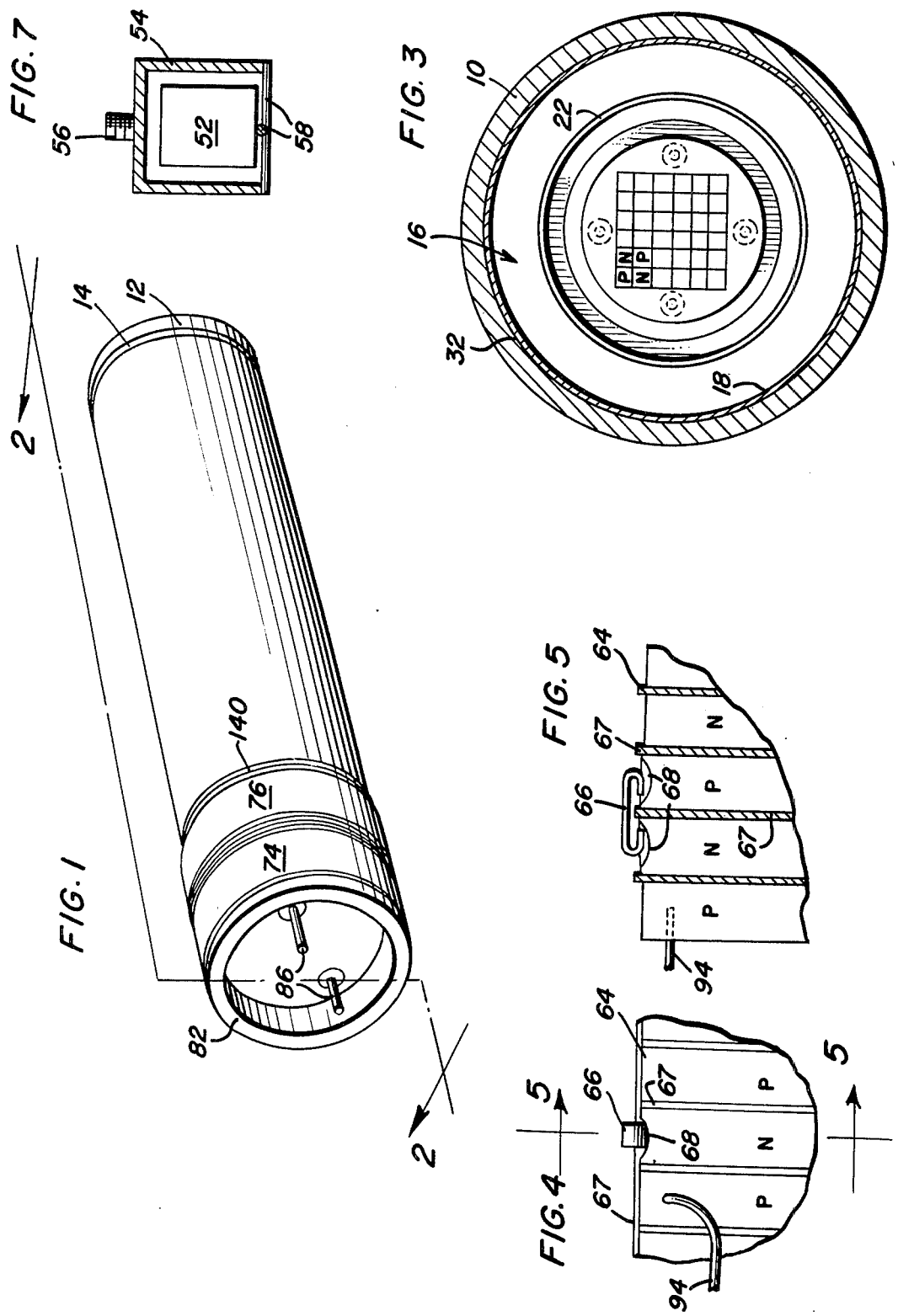
FIG. 1 is a view in perspective of the novel microwatt thermoelectric generator.
Figure 2:
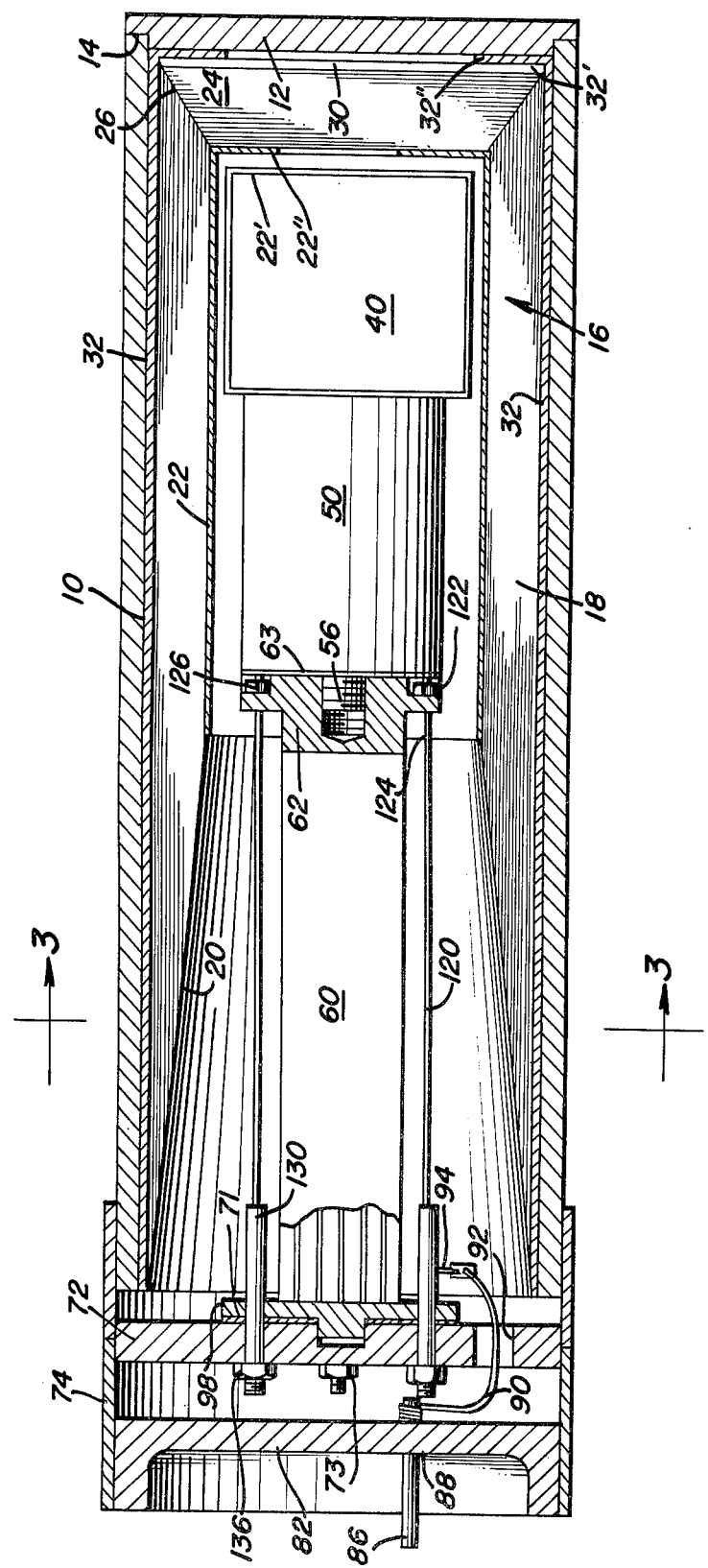
FIG. 2 is a vertical section of FIG. 1 taken along line 2—2 of FIG. 1.
Figure 6:
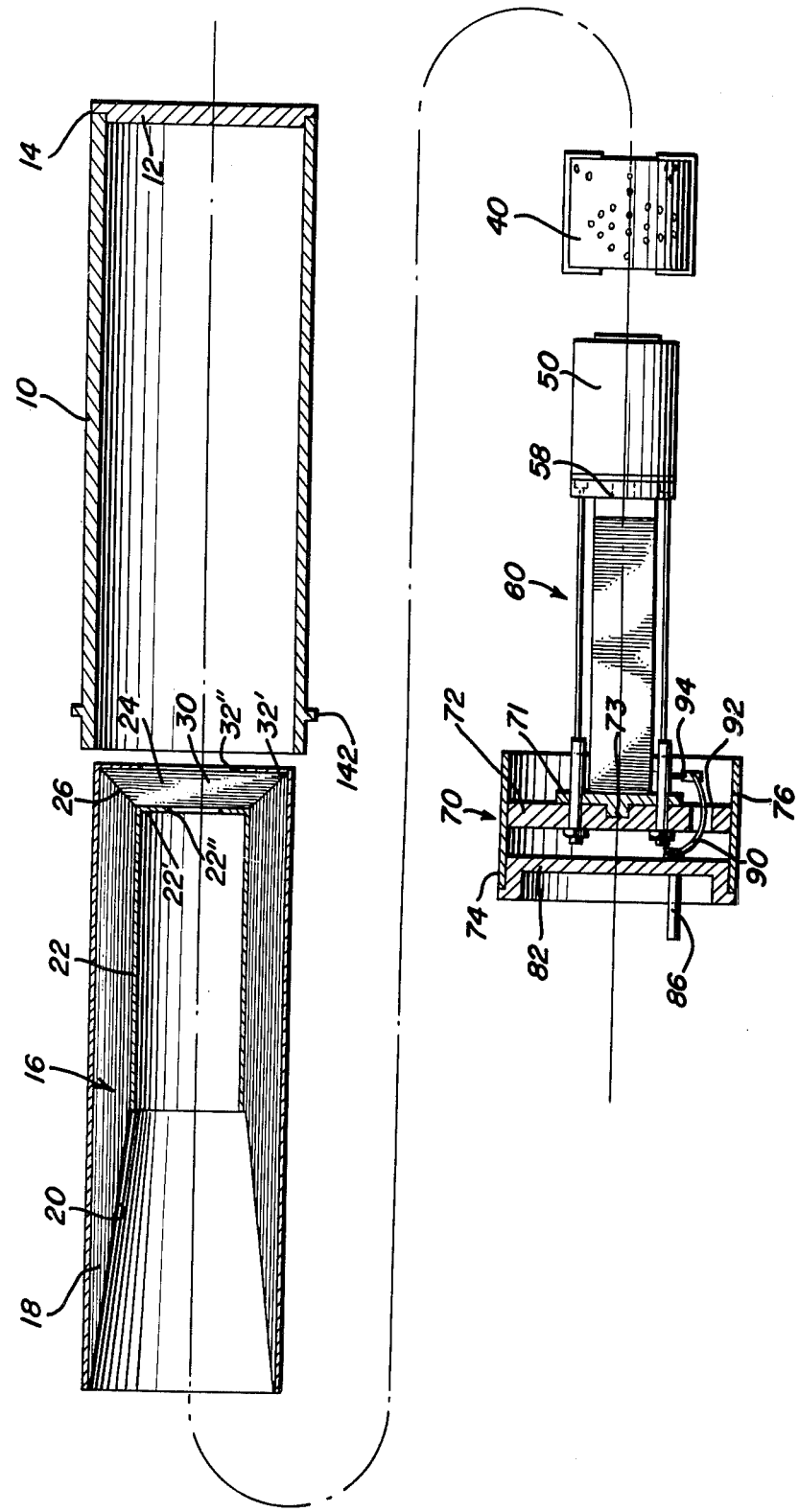
FIG. 6 is an exploded perspective view illustrating the manner of assembly.

Referring to the drawings, an embodiment of the invention will be described in detail. The novel microwatt thermoelectric generator of the present invention is capable of an electrical power output of 300 – 400 microwatts at approximately 0.3 volts using a nuclear power source equivalent to approximately 50 milliwatts of thermal energy. This is generally equivalent to 1/10 gram of a suitable form of plutonium (oxide). The generator consists of a cylindrical outer casing 10 which is closed at one end by a cap 12 by means of a weld joint 14. The joint is formed by electronic beam welding or equivalent means to provide a vacuum-tight seal between the casing 10 and the cap 12. Within the casing 10 is positioned a foil insulation package generally designated by the reference numeral 16. The foil insulation package 16 which includes a spirally wrapped foil 18 which is tapered as indicated by reference numeral 20 from about the midpoint of the casing 10 to the end of the casing opposite the cap 12. The foil 18 is tapered to prevent the hotter portions (inner wraps) from conducting heat from the hot side to the cold side of the generator. It has been discovered that conduction of heat down the foils could constitute a substantial parasitic loss. The foil 18 laid out is trapezoidal in configuration and is wrapped about an inner can 22 a number of turns until it has reached a predetermined thickness. During this time, a series of disks 24 of increasing diameter are placed against the end 22' of the inner can 22 registering with the turns 18 of the foil insulation package along the bevel line 26. It will be noted that the end 22' of the inner can 22 is provided with a central opening 22'', the purpose of which will become more apparent hereinafter. When a suitable number of foil turns 18 and disks 24 has been assembled about the inner can 22, a plate 30 is placed against the outer disk 24 and an open-mouthed outer can 32 is fitted over the platte 30 and encloses the foil insulation package 16. The outer can 32 is provided at its end 32' with an opening 32''.

The foil insulation, approximately ½ mil thick, is comprised of any heat reflecting material, such as platinum, aluminum or stainless steel, and is provided with a coating of zirconia. The coating is an extremely think layer of approximately 0.1 mils thickness or less. As the foil is wrapped about the inner can 22, every fifth wrapping 18 is tabbed and spot welded or tacked to a corresponding numbered disk 24 to provide the insulation package with structural integrity and to make it easier to handle during assembly. The disks 24 are similar in nature and comprise ½ mil foils provided with the same zirconia coating. As already noted, the foil disks 24 increase in diameter from the inside to the outside to provide the bevel contact line 26 with the foil wrappings 18.

The insulation package is effective only in a vacuum and therefore a hard vacuum environment is required. Above approximately $10^{-3}$ torr or 10 microns pressure, the insulating properties of the package begin to degrade.

Located at the innermost part of the foil insulation is a getter assembly designated as 40. The getter assembly consists of a tantalum can provided with a plurality of holes in which is located a barium powder pellet. The can may be composed of other metals or alloys such as aluminum, titanium or stainless steel.

What has been described so far comprises one of the two major subassemblies of the microwatt thermoelectric generator and consists of three main components, namely, the outer casing 10 and end closure 12; the foil insulation package comprised of the wrappings 18 and the disks 24; and the getter assembly comprised of the perforated can with the barium pellet contained within. Since the microwatt thermoelectric generator is to be implanted within a human body with the electronic device it powers and since the effectiveness of the overall assembly is dependent in large measure upon maintenance of a vacuum within the casing, it is important that the getter have sufficient capacity to maintain the vacuum integrity for a long period of time and to be able to getter gases at a rate in excess of that at which they are produced. One of the important properties of the getter in this respect is the exposed surface area and, for this reason, although a solid barium pellet may be employed, it is believed that significant improvement is obtainable using a porous barium pellet or other configuration having high surface to volume ratio. In this respect, the density of the pellet is of importance due to the correlation with porosity.

The other subassembly of the generator comprises generally a fuel capsule 50, a thermopile assembly 60 and end cap 70.

The fuel capsule assembly consists of double cans 52 of a suitable containment material such as HASTELLOY C-276, a nickel base superalloy manufactured under this trade name by Stellite Division of Cabot Corporation of Kokomo, Ind. within which is positioned a suitable quantity of plutonium oxide having the desired and preferred properties and characteristics. The welded sealed double cans 52 are positioned loosely within an open skirt 54 comprised of stainless steel material which is provided on its closed end with a stud 56. The open cylinder 54 has a wall thickness of approximately 25 mils and two wires 58 are attacked across its open end in cruciform pattern for the purpose of holding the double cans within the cylinder 54.

The stud 56 of the cylinder 54 is threaded into an aluminum plate 62 serving as the hot plate of the thermopile assembly 60. Between the aluminum plate 62 and the outer surface of the end of cylinder 54 is a 4 mil stainless steel spacer 63 comprised of a hub surrounding stud 56 and having radial arms projecting from the hub. The aluminum plate 62 serves as the hot plate or hot end of the thermopile assembly which is shown in detail in FIG. 3, and the plate 62 has ax oxide coating on its face contacting the thermopile to insulate same therefrom.

In lieu of the arrangement shown and described for the fuel capsule 52, the open-ended can 54 can be eliminated and the capsule 52 connected directly to the getter assembly 40. The hot plate 62 will, in this form, simply be brought into proximity with the fuel capsule 52 and either loosely physically contact same or be separated therefrom by a small thermal gap.

The thermopile assembly consists of a series of elongated semiconductor thermoelectric elements 64, such as P-and N-type bismuth telluride, with the elements 64 being stacked together in a parallel array with the P and N elements alternating. The semiconductor thermoelectric elements are 15 mils square and about ¾ inch long with the stack or array comprised of such elements. The elements within the array are separated by 5 mil polyimide films 67 such as are obtained commercially under the trade name KAPTON from E. I. du Pont de Nemours & Co. The interconnection within the thermopile, that is the shoes 66 to connect adjacent elements so that the thermopile constitutes a single series-connected electrical path, is comprised of shoes which have been alloyed into the end faces of the elements as shown in FIGS. 4 and 5. The procedure for making the connection consists of laying lengths of wire or bar (straps) across the two elements to be interconnected and then applying a capacitive discharge or similar high energy heat source through spaced locations at which it is desired to alloy the wire and form the alloy contact 68. This technique is known as weld brazing in the art. The bismuth telluride beneath the wire has a melting point considerably below that of the wire. The heat is applied to the wire and not to the bismuth telluride until the metal of the wire alloys with the bismuth telluride by forming an eutectic or other phase molten zone. The wire or bar is folded at either end before weld brazing to raise the portion of the shoe that passes over the insulating film 67. The final configuration of the alloy contact and the interconnection made by the shoe is illustrated in FIG. 5. The wire material is preferably palladium, although gold, nickel, gold-plated nickel, and gold 92%-palladium 8% may be used, but not as effectively.

The semiconductor thermoelectric materials suitable for practicing the invention are $Bi_2Te_3$, $Sb_2Te_3$, $Bi_2Se_3$, $Sb_2Se_3$, and solid solutions and alloys of the foregoing such as $Bi_2Te_3$ — $Sb_2Te_3$ (P-type), $Bi_2Te_3$ — $Sb_2Te_3$ (N-type), $Bi_2Te_3$ — $Bi_2Se_3$ (N-type), and $Bi_2Te_3$ — $Bi_2Se_3$ (P-type), all with appropriate dopants. To produce N-type conductivity, the following dopants are appropriate: AgCl, AgBr, AgI, $CuBr_2$, $SbCl_3$, Cu, Ag, Te, and I. To produce P-type conductivity, the following dopants are appropriate: Bi, Pb, Na, Cd, In, Sn, Sb, and Ni.

A cold plate 71 is provided at the other end of the thermopile. The faces of the aluminum plates 62 and 71 which bear against the thermopile are provided with an oxide coating which maintains electrical isolation while permitting desirable heat transfer. The cold plate 71 is provided with a central boss 73 which is received within a recess 73' defined centrally in the inside surface of a bearing plate 72. Outer rings or cylinders 74 and 76 of titanium are each welded at one end to the bearing plate 72 in a vacuum-tight manner with the weld joints being indicated by the reference numerals 78 and 80, respectively. Rings 74 and 76 may be composed of other suitable materials. The other end of the cylinder 74 is welded to an end closure plate or header of niobium 82 by a vacuum-tight joint 84. An electrical outlet or terminal 86 composed of niobium passes through the end plate 82 and is sealed in an alumina plug 88 which, in turn, is sealed in end plate 82. Alumina plug 88 is annular in configuration and is prepared by washing a molymanganese slurry on the inner and outer surfaces of the plug 88 and oxidizing in wet hydrogen at 1400° C. to alloy with the alumina. A nickel coating is placed over both surfaces of the niobium header 88 and terminal 86 to be attached to the alumina plug 88. A silver-coppper or gold-copper braze is used to connect nickel coated niobium parts to the alumuna plug 88.

The use of a niobium header, niobium lead and alumina plug seal is considered to be a unique feature as these materials have good compatibility regarding expansion characteristics. One or two such electrical outlets 86 may be employed depending upon design considerations. If two are employed, then both pass through the plate 82 and are sealed within an alumina plug as described. If only one lead passes out of the casing, then the other lead is connected between the thermopile and the casing 10.

In a preferred embodiment of the header, the end plate 82 is composed of tantalum. This combination, tantalum-alumina-niobium, gives superior results as on cool-down, the area of greatest concern and technical difficulty; the tantalum seems to shrink faster than the alumina or niobium lead and thereby maintains substantial pressure directed radially inward toward the center of the header.

The interconnection between the outlet 86 and the thermopile is achieved by means of a gold palladium lead 90 connected at one end to the output 86, which lead 90 passes through a hole 92 formed in the bearing plate 72 and is connected to a palladium wire 94 — palladium being the preferred material — which, in turn, is connected to an appropriate end of one of the semiconductor thermoelectric elements. The connection is achieved by drilling a small hole in the selected element and inserting the wire and then brazing by heating the wire with a plasma torch, welding by a capacitive discharge or similar weld-brazing technique so that the palladium alloys with the bismuth telluride within the hole. The second electrical connection is made to another appropriate semiconductor thermoelectric element in the same fashion and is either connected to another outlet 86 via a wire 90 or is connected to the casing via a wire 90. The connections to the thermopile by means of the wires arefurther enhanced by potting the connections with epoxide cement to strengthen the joint and prevent a breaking of the lead or the alloy contact due to stress.

In addition to the foregoing, the thermopile is positively connected to the plates 62 and 71 by means of an epoxide cement or glue having matching characteristics to the polyimide film spacers in the thermopile. The epoxide cement film that effects this connection is about one mil in thickness and serves the purpose of eliminating any gap between the thermopile and the plates 62 and 71. As the interior of the container 10 is to be maintained under a severe vacuum (at least $10^{-3}$ torr), it is essential that the heat transfer through the thermopile and between the plates be maximized. Any gap in this thermal path would pose severe thermal resistance due to the vacuum. Similarly, an annealed gold foil 98 is interposed between the cold plate 71 and the bearing plate 72 and between the hot plate 62 and the skirt plate 63 or capsule 50 for the same reason. The gold foil 98 is 2 mils thick and due to its ductility will serve to fill the gap between the aluminum plate 71 and the bearing plate 72 and between members 62 and 63 or 50 caused by surface disparities.

The thermopile assembly also includes a support harness to maintain a compressive load on the thermoelectric elements. This support harness is comprised of a series of four equally spaced tension wires 120 about sixmils in diameter to minimize parasitic heat losses. The wires are composed of 94.5 percent titanium, three percent aluminum and 2.5 percent vanadium. The purpose of this particular composition is to provide the highest possible structural strength with the lowest possible thermal conductivity as the tension wires provide a direct path between the hot and cold plates and, therefore, tend to serve as a thermal bypass to the thermopile. The hot plate 62 is suitably recessed as indicated by the reference numeral 122 at four equally spaced locations about its periphery on the side of the plate 62 remote from the thermopile. Axial bores 124 are formed in the plate 62 extending from the recesses 122. One end of the tension wires 120 passes through axial bores 124 and is brazed into bores formed in stainless steel caps 126 using a copper-nickel alloy. In a specific example, the wires used have a strength for loadings up to 125,000 pounds per square inch and a thermal conductivity of 4.6 BTU per foothour-degree Fahrenheit. The ratio of wire strength to thermal conductivity is greater than 250,000 and preferably 300,000 or greater.

Externally threaded studs 130 provided with a central bore receive the other ends of the tension wires 120 within their central bores, and these other ends are similarly fixed inside the bores of the studs 130 by the intermediary of a copper-nickel braze. The threaded studs 130 pass through holes in the cold plate 71 and the bearing plate 72 and receive on their ends remote from the thermopile threaded nuts 136. The nuts are tightened to apply a compressive loading to the thermopile by tensioning the wires 120. As an example, the wires 120 are loaded to approximately 1.2 pounds per wire to place a total preload on the pile of 4.8 pounds.

In an alternative and preferred embodiment of the invention, the tension wires are fabricated by threading the ends of 0.03-inch diameter titanium alloy wires containing 3% aluminum and 2.5% vanadium and then chemically milling the center section of the wires to a diameter of about 0.006 inches. The threaded ends are held by nuts directly in recesses 122, and nuts 136 are used to tighten down the harness against the bearing plate 72.

To assemble the microwatt thermoelectric generator, the containter 10 is first welded to the end cap 12, and then the foil insulation package consisting of the wrappings 18 and disks 24 are inserted within the container 10 as previously described. Container 10 is comprised of tantalum, titaniumor niobium, as are the bearing plate 72 and end plate 82. Likewise, the outlet or lead 86 is comprised of niobium, tantalum or titanium. Next, the getter assembly 40 comprised of the porous barium pellet contained within the perforated tantalum can having a wall thickness of 5 mils is inserted into the container and foil insulation package. The container is then placed in a vertical position with the open end upward and within an electron beam welding apparatus located in a vacuum chamber. The vacuum is drawn down to the desired level of $10^{-6}$ mm Hg, and then the barium pellet is heat treated in a novel manner to activate same and greatly enhance its getter properties. The barium pellet prior to this time has been maintained in an inert gas atmosphere (argon), and the surfaces are saturated with adsorbed argon and other gases. Accordingly, a heater is lowered into the container and placed in close proximity with the greater assembly and the temperature elevated to about 800° F. where it is maintained for about two hours to outgas the barium. This procedure activates the barium and renders its surfaces more active, thereby greatly improving its efficiency to getter gases.

In the meantime, the other subassembly consisting of the fuel capsule, and the thermopile assembly, including its hot and cold plates, is outgassed at a temperature of about 500° F. to about 550° F. for 24 hours to one week and then assembled, together with the harness, the bearing plate 72, and end plate 82, and rings 74 and 76, the tension wires 120 having been brought to their proper load settings during this assembly.

This other subassembly is then checked for electrical resistance to be certain the path through the thermopile is of proper electrical resistance, for example, about 60–90 ohms. As the thermoelectric elements are very small and brittle, micro-cracks are present which cannot be detected visually but affect the pile resistance raising it to 1000 or 2000 ohms. The heating to 500° F. or above for 24 hours or longer serves to heal some of the micro-cracks by diffusion and improves shoe bonds, but usually the pile resistance is still too high. It has been discovered that if the pile is subjected to pressure endwise and a capacitive discharge (about 2.0 watt-seconds or higher) the irregularities of the pile heal, and the resistance drops to its proper value. The capacitive discharge is in the form of a high current pulse of short duration (milliseconds) and has been found effective to heal defects and irregularities of the pile.

The components of this other subassembly have, previous to assembly of the tension wire harness, been subjected to an outgassing at a temperature of about 500° F. This is an extremely advantageous procedure as it serves to minimize the load upon the getter and enables long and more efficient getter life. These subassembly components may be outgassed at such an elevated temperature because the shoes and electrical contacts have been connected to the thermopile in a special way and because of the thermal stability of the component materials. For example, the various alloy contacts made to the thermopile have high temperature, as well as non-poisoning characteristics, and, therefore, the thermopile may be subjected to this elevated temperature without danger that these contacts will be dislodged or deleterious diffusions will occur.

The other subassembly, prepared as described, is then brought into the first subassembly by lowering, fuel capsule first, into container 10. The final weld and sealing of the unit occurs at the joint 140 between the free end of the ring or cylinder 76 and the open end of the container 10. As will be noted, the cylinder 76 slides over the end of the container 10, and the weld joint is made between the edge of the cylinder 76 and a flange 142 defined by the container 10. As with all other weld joints, this one must be vacuum tight.

Figure 8:
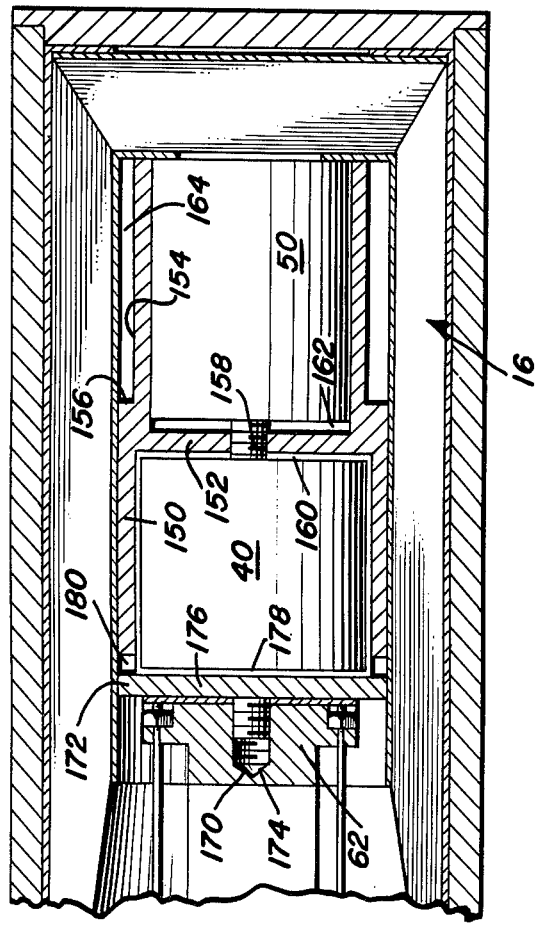
FIG. 8 is a sectional view like FIG. 2 showing a preferred arrangement for the fuel capsule and getter assembly.

The preferred arrangement for the fuel capsule and getter is illustrated in FIG. 8. The fuel capsule 50 and getter assembly 40 are reversed inside the foil insulation package 16, and the getter assembly 40 is positioned between the fuel capsule 50 and thermopile assembly 60. In detail, a skirt or cylinder 150 is provided having a central transverse web 152 and a recessed part 154 defining a shoulder 156. The fuel capsule 50 is provided with a stud 158 which is received in a threaded bore 160 formed in web 152. A gold foil 162 is located between the fuel capsule 50 and web 152 to preclude a thermal gap. Insulating foils 164 like those of insulation package 16 are stacked in the recess defined by part 154. The getter assembly 40 is contained within the skirt 150. This configuration gives the highest operating temperature (about 400° F.) for the getter assembly 40 and, therefore, provides the best gettering capability. The bottom of the thermopile (the hot plate 62) is provided with a threaded bore 170, and a skirt plate 172 with threaded stud 174 is connected to the hot plate 62 with a gold foil 176 interposed therebetween to prevent a thermal gap. The skirt plate 172 is separated from the end of the getter assembly by a gap 178 of 0.050 inches to provide a thermal shunt and essentially limit heat transfer to that heat which radiates from getter 40 and the top of cylinder 150. Located between the cylinder 150 and skirt plate 172 is a stack of insulating annular foils 180 like those of insulation package 16.

The microwatt thermoelectric generator assembled as described has several distinct advantages. First, the construction of the insulation and the thermopile, as well as the other components, enables the use of the smallest possible fuel supply to obtain the largest possible electrical output. As noted previously, using a fuel supply of approximately 50 milliwatts of thermal energy, the generator is able to provide an output of approximately 350 microwatts at 0.3 volts. The getter assembly must operate at the highest possible temperature in order to work at the best possible efficiency. On the other hand, the thermopile and outer case must reject heat at a relatively lower temperature for the simple reason that the device will be in the human body. The cold end of the thermopile, the cold plate 71, should be about 100° F. to match normal body temperature. The power generation in the thermopile requires about 100° F. of temperature difference and, therefore, the hot plate 62 should be operating at about 200° F.

If the internal assembly were efficiently thermally interconnected, the getter assembly would be functioning close to 200° F., and its efficiency would be greatly impaired. Thus, the getter assembly should be functioning at temperatures above 250° F. and more preferably at about 400° F. as noted in connection with the arrangement of FIG. 8. Coupled with this information is the further fact that the fuel capsule itself can generate a maximum temperature level dependent upon the limited quantity of nuclear fuel contained in the double cans 52.

To harmonize these various features and to achieve the maximum effect, the generator has been judiciously designed so that the getter will operate at a relatively high temperature and yet the hot end of the thermopile will be maintained at the preferred 200° F. level. These results are achieved by the technique of locating the fuel container 52 within the cylinder 54 so that a small space exists, or a loose mechanical contact is present, between the fuel container 52 and the end of the cylinder 54 or by relating the fuel capsule 52 to the getter assembly 40 and leaving a thermal gap between the fuel capsule 52 or getter assembly 40 and the hot plate 62. This will allow the fuel container to operate at a higher temperature than would be possible if there would be good thermal contact. Also, in one form, the stainless steel spacer 63 inserted between the cylinder 54 and the hot plate 62 will provide further thermal resistance to assure the proper operating temperature of the hot plate 62. On the other hand, the getter will be exposed to the higher temperature of the capsule, and, since it is surrounded by maximum insulation, its operating temperature will be above 250° F.

It will thus be evident that a thermal drop has been purposely introduced between the fuel container 52 and the hot plate 62, and, although this would seem to be inconsistent with efficient operation of a thermoelectric generator, nevertheless, in the circumstances of the present case, this turns out to be necessary for efficient operation of the generator for the reasons explained.

Although the present invention has been described with reference to a preferred embodiment, various changes and modifications will be evident to those skilled in the art which do not depart from the inventive concepts taught herein.

What is claimed is:

1. A novel header for use in nuclear applications comprising a plate containing at least one bore, the inside surfaces of which carry a nickel coating, an alumina plug in said bore, said alumina plug sealed in said plug by means of a braze, and an integral niobium terminal passing through said plug, said niobium terminal carrying a nickel coating on at least those surfaces where said terminal passes through said alumina plug, said niobium terminal being sealed in said plug by means of a gold-copper or silver-copper braze heated to about 930°C.

2. Novel header according to claim 1 in which said plate defines two bores with a terminal passing through each via alumina plugs.

3. A novel header according to claim 1 wherein said plate is niobium.

4. A novel header according to claim 1 wherein said plate is composed of a material selected from the group consisting of tantalum and its alloys.

5. A novel header according to claim 1 wherein the inner and outer surfaces of said alumina plug are formed by an alloy of alumina with molybdenum and manganese.

6. A vacuum tight seal for use in nuclear applications comprising: a substantially flat baseplate made from niobium, tantalum or tantalum alloys, said baseplate having a bore passing therethrough, the surfaces of said bore carrying a nickel coating; and an integral niobium electrical terminal passing through said bore, said niobium terminal adapted to make an electrical connection at each end thereof, said niobium terminal carrying a nickel coating; said apparatus further characterized in that said niobium terminal is sealed in said baseplate by means of an alumina plug whose inner and outer surfaces are composed of an alloy of alumina, manganese and molybdenum, the outer surfaces of said alumina plug being sealed to the nickel coated surfaces of said bore by means of a silver-copper or gold-copper braze heated to about 930°C. and the inner surfaces of said alumina plug being sealed to the nickel coated surfaces of said niobium terminal by means of a silver-copper or gold-copper braze heated to about 930°C.

7. The device of claim 6 wherein the outer surfaces of said alumina plug are generally similar in configuration to the cross section of said bore, and further wherein the inner surfaces of said alumina plug are generally similar in configuration to the cross section of said niobium terminal.

* * * * *

UNITED STATES PATENT OFFICE
CERTIFICATE OF CORRECTION

PATENT NO. : 3,936,320
DATED : February 3, 1976
INVENTOR(S) : David Earl Goslee & Harold Newton Barr It is certified that error appears in the above–identified patent and that said Letters Patent are hereby corrected as shown below:

Column 3, line 33, change "think" to --thin--;

line 47, change "10" to --1--.

Column 5, line 43, change "molymanganese" to --moly-manganese";

line 50, change "alumuna" to --alumina--.

Column 6, line 2, change "gold palladium" to --gold-palladium--;

line 19, change "arefurther" to --are further--;

line 65, change "foothour-degree" to --foot-hour-degree--.

Column 7, line 27, change "titaniumor" to --titanium or--.

Signed and Sealed this

Thirtieth Day of November 1976

[SEAL]

Attest:

RUTH C. MASON
Attesting Officer

C. MARSHALL DANN
Commissioner of Patents and Trademarks